(12) United States Patent
Suda

(10) Patent No.: US 9,310,473 B2
(45) Date of Patent: Apr. 12, 2016

(54) METHOD FOR EVALUATING IMAGE QUALITY OF ELASTIC IMAGE, AND ULTRASONIC DIAGNOSTIC APPARATUS

(75) Inventor: Masahiro Suda, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 7 days.

(21) Appl. No.: 13/579,331

(22) PCT Filed: Feb. 17, 2011

(86) PCT No.: PCT/JP2011/053319
§ 371 (c)(1),
(2), (4) Date: Aug. 16, 2012

(87) PCT Pub. No.: WO2011/102401
PCT Pub. Date: Aug. 25, 2011

(65) Prior Publication Data
US 2012/0321165 A1  Dec. 20, 2012

(30) Foreign Application Priority Data
Feb. 17, 2010  (JP) .................. 2010-032991

(51) Int. Cl.
*G06K 9/46* (2006.01)
*G01S 7/52* (2006.01)
*A61B 8/08* (2006.01)

(52) U.S. Cl.
CPC ............. *G01S 7/5205* (2013.01); *A61B 8/485* (2013.01); *A61B 8/5207* (2013.01); *A61B 8/5269* (2013.01); *G01S 7/52042* (2013.01); *G01S 7/52074* (2013.01)

(58) Field of Classification Search
CPC .. G01N 29/323; A61B 8/5269; A61B 8/5276; A61B 8/5223; G06T 7/0012
USPC .......................................................... 382/131
See application file for complete search history.

(56) References Cited

U.S. PATENT DOCUMENTS

| 6,558,324 B1 * | 5/2003 | Von Behren et al. ......... 600/440 |
| 2004/0111028 A1 * | 6/2004 | Abe et al. ..................... 600/437 |

(Continued)

FOREIGN PATENT DOCUMENTS

| JP | 2004-351062 | 12/2004 |
| JP | 2005-118152 | 5/2005 |

(Continued)

OTHER PUBLICATIONS

Ashbindu Singh (1989) Review Article Digital change detection techniques using remotely-sensed data, International Journal of Remote Sensing, 10:6, 989-1003, DOI: 10.1080/01431168908903939.*

(Continued)

*Primary Examiner* — Chan Park
*Assistant Examiner* — Geoffrey E Summers
(74) *Attorney, Agent, or Firm* — Brundidge & Stanger, P.C.

(57) ABSTRACT

Disclosed in an ultrasonic diagnostic apparatus for appropriately evaluating the image quality of a elastic image with high reliability and accuracy, the ultrasonic diagnostic apparatus including: a probe (12) that transmits and receives ultrasonic waves to and from an object; an elasticity information calculating unit (32) that calculates elasticity information on the basis of the ultrasonic waves received by the probe (12); an elastic image constructing unit (34) that generates an elastic image on the basis of the elasticity information; an image display device (display) (26) that displays the elastic image; and an elastic image evaluating unit (40) that detects the fluctuation cycles in the elasticity information, finds the fluctuation patterns in the elasticity information for each predetermined section in the fluctuation cycles, and evaluates the stability of the elastic image on the basis of the fluctuation patterns.

10 Claims, 6 Drawing Sheets

(56) References Cited

U.S. PATENT DOCUMENTS

| | | |
|---|---|---|
| 2007/0032726 A1* | 2/2007 | Osaka et al. ............ 600/459 |
| 2008/0064956 A1* | 3/2008 | Jeong et al. ............ 600/438 |
| 2008/0103392 A1* | 5/2008 | Seki et al. ............ 600/437 |
| 2008/0269606 A1* | 10/2008 | Matsumura ............ 600/438 |

FOREIGN PATENT DOCUMENTS

| | | |
|---|---|---|
| JP | 2007-090003 | 4/2007 |
| JP | 2007282932 A | 11/2007 |
| JP | 2008-073144 | 4/2008 |
| JP | 2008-126079 | 6/2008 |
| JP | 2010-017585 | 1/2010 |
| WO | 2006/040967 | 4/2006 |
| WO | 2007/138881 | 12/2007 |

OTHER PUBLICATIONS

International Search Report from International Application No. PCT/JP2011/053319 mailed Mar. 22, 2011.
Foreign Office Action (including English Translation).

* cited by examiner

METHOD FOR EVALUATING IMAGE QUALITY OF ELASTIC IMAGE, AND ULTRASONIC DIAGNOSTIC APPARATUS

FIELD OF THE INVENTION

The present invention relates to a method for evaluating image quality of elastic images and an ultrasonic diagnostic apparatus that executes the method thereof.

DESCRIPTION OF RELATED ART

In making a diagnosis of a tumor, etc. in a target region of interest using an ultrasonic diagnostic apparatus, elasticity information which shows hardness or softness of the biological tissue of a tumor, etc. (for example, information such as the strain or elasticity modulus) is significant. In order to obtain an elastic image, first a cross-sectional surface including a region of interest is scanned in a periodic basis with an ultrasonic beam while the compression to be applied to the region of interest by a probe via the body surface of an object is changed on a periodic basis, and plural sets of RF signal frame data are generated by receiving and processing the ultrasonic wave which is reflected from the biological tissue in the scanned surface.

Next, two sets of RF signal frame data acquired with different pressure are selected from among the plural sets of RF signal frame data, and the displacement (displacement vector) of the biological tissue is acquired between the two sets of RF signal frame data. Then the distribution of elasticity information which represents the hardness or softness of the biological tissue in the respective portions of the cross-sectional surface including the region of interest is obtained on the basis of the acquired value of displacement, and the elastic image showing the distribution of the elasticity information is displayed on a display such as a monitor.

The elastic image is displayed on a monitor, etc. in the way that a hard region can be easily recognized in accordance with the strain or the elasticity modulus of the biological tissue, for example by giving a hue such as red or blue, as disclosed in Patent Document 1. In this manner, the extensity or size of a malignant tumor such as cancer can be easily diagnosed.

Incidentally, when an examiner manually presses an object using a probe, from the initial condition in which a certain amount of initial pressure (includes zero) is applied by the probe from the body surface of the object, the examiner repeats the operation by moving the probe in the pressing direction toward a region of interest and in the releasing direction away from the region of interest. In other words, the examiner repeats increasing and decreasing of pressure on the basis of the initial condition that pressure is applied on a region of interest. By consecutively obtaining the RF signal frame data in the process of increasing and decreasing pressure, the displacement in the respective portions of the biological tissue is acquired between the two sets of RF signal frame data having different acquisition times, i.e. different pressure values.

However in the manual operation of increasing and decreasing the pressure, it is difficult to avoid fluctuation in the pressing operation such as the intensity of stroke, the velocity and the direction in the pressing and releasing of a probe. Accordingly, the images obtained with improper pressing operation are often mixed among the plural elastic images that are consecutively obtained.

Given this factor, in the case of making a diagnosis by referring to elastic images, the obtained elastic images have been once stored in a memory such as a cine memory or an external storage media and regenerated for making a diagnosis. That is, the plurality of obtained elastic images are once stored in a memory and the elastic images in the memory are regenerated and displayed on a monitor by list display or scroll display, so that an examiner can select the elastic image which is appropriate for making a diagnosis while observing the regenerated images.

However, there is no guarantee that the selected elastic images always have sufficient image quality, since the examiner selects them objectively. Also, in the process of selecting the elastic image for making a proper diagnosis, the rewinding operation of the generated images and making decision to select images can consume much of the examiner's time.

In order to solve such problems, Patent Documents 2 and 3 propose a technique to obtain the degree of noise included in the elastic images on the basis of various data acquired in the process of collecting the elasticity information and select the image to display.

PRIOR ART DOCUMENTS

Patent Documents

Patent Document 1: JP-A-2000-60853
Patent Document 2: JP-A-2005-118152
Patent Document 3: U.S. Pat. No. 6,558,324

However, in accordance with the method for evaluating image quality of elastic images disclosed in Patent Documents 2 and 3, while the image quality of elastic images can be evaluated, the reliability and accuracy in image quality evaluation of elastic images still need to be improved.

The objective of the present invention is to evaluate image quality of elastic images properly with high reliability and accuracy.

BRIEF SUMMARY OF THE INVENTION

In order to achieve the above-described objective, the method for evaluating image quality of elastic images related to the present invention which:
  loads plural sets of RF signal frame data via a probe;
  calculates plural sets of displacement frame data which represent the displacement distribution on the basis of the plural sets of RF signal frame data;
  calculates plural sets of elastic frame data which represent the distribution of elasticity information on the basis of the plural sets of displacement frame data; and
  evaluates the image quality of plural elastic images in the scanned plane generated on the basis of the respective sets of elastic frame data,
  is characterized in:
  detecting the fluctuation cycle of the displacement of the plural sets of displacement frame data or the elasticity information of the plural sets of elastic frame data;
  obtaining the feature quantity of the fluctuation pattern of the displacement or the elasticity information for each predetermined section of the fluctuation cycle; and
  evaluating the image quality of the elastic images generated from the elastic frame data corresponding to the respective sections on the basis of the change in the feature quantity.

In the operation for manually and periodically changing the pressure to be added by a probe, it is difficult to avoid, in the pressure added to a region of interest of an object, the fluctuation of pressing operation in the intensity of a stroke, velocity or direction of pressing and releasing operation. Therefore, the elastic images with much noise that are obtained by inappropriate pressing operation are mixed in with the consecutively obtained plurality of elastic images. Even when the pressure is added mechanically, the same problem occurs due to improper operation of the device.

The present inventors have learned that the elastic images obtained by repeating the similar and stable pressing operation tend to have stable image quality with less noise.

Given this factor, the present invention detects the fluctuation cycle of the displacement of plural sets of displacement frame data or the elasticity information of the plural sets of elastic frame data. This fluctuation cycle corresponds to the pressing operation. It means therefore that when the pattern of the detected plural fluctuation cycles is similar and continued, the repetition of pressing operation is stabilized.

The present invention is characterized in that the stability of pressing operation is evaluated on the basis of the fluctuation pattern of the displacement of displacement frame data or the elasticity information of elasticity frame data, since the elastic frame data acquired by the result of pressing operation directly influence the image quality of elastic images. Further, in addition to the stability of pressing operation, the present invention evaluates the image quality of elastic images by executing image-quality evaluation as disclosed in JP-2005-118152 (Patent Document 2). In this manner, it is possible to evaluate the image quality of elastic images in a stable manner and select elastic images with high reliability and accuracy that are appropriate for making a diagnosis.

In concrete terms, the present invention detects the fluctuation cycle of the displacement of the plural sets of displacement frame data or the elasticity information of the elastic frame data, acquires the feature quantity of the fluctuation pattern of the displacement or the elasticity information for each predetermined section of the fluctuation cycle (for example, a half cycle), acquires the difference between the feature quantity of a certain section and the feature quantity of another single or plural sections which are detected prior to the certain section, and evaluates, on the basis of the difference of the feature quantities, the stability of pressing operation which influences the image quality of elastic images. That is, the image quality of the elastic image generated from the elastic frame data corresponding to the certain section is evaluated. Further, the image quality of elastic images is evaluated by executing the image-quality evaluation method as disclosed in JP-2005-118152 (Patent Document 2). A half cycle here means from an inflection point to an inflection point of one fluctuation cycle, or in the case of a fluctuation cycle of strain, from level 0 to the next level 0 of the strain.

Also, the average value of the displacement of the biological tissue in the same set regions or regions of interest as set in the plural sets of displacement frame data, or the average value of the strain or the elasticity modulus of the biological tissue in the same set regions or region of interests as set in the plural sets of displacement frame data can be used for fluctuation cycles. Also, any of the average value, the standard deviation, the dispersion or the area (for example, accumulated strain) of the fluctuation of displacement or elasticity information in the respective sections can be used for the feature quantity of the fluctuation pattern in the displacement or elasticity information in the respective sections.

In the case in which the average value of the strain in the biological tissue in a region of interest is used for the elasticity information of the elastic frame data, the fluctuation cycle of the strain average value is the continuation of half cycles which fluctuate in plus and minus on the basis of 0% strain. Therefore, the difference of the absolute values of the feature quantity or the statistical values which are not related to either plus or minus is to be used for the difference of the feature quantities of the strain fluctuation in the respective sections. In the present invention, not only the average value of the strain but also the average value of the elasticity modulus (for example, the Young's modulus) of the biological tissue in a region of interest can be used for the elasticity value. In place of these statistical feature quantities, the statistical feature quantities showing the stability of the fluctuation pattern of half cycles can also be used.

Further, by extracting a certain section in which the difference of the feature quantities of the fluctuation pattern is smaller than a predetermined threshold value, the elastic image which is generated on the basis of the elastic frame data of the extracted section can be evaluated as having high image quality. In this case, the proportion of the noise region included in the elastic image is acquired on the basis of the plural sets of elastic frame data in the extracted section and the elastic frame data having the smallest proportion of the noise region is selected in the one extracted section, and the elastic image corresponding to the selected frame data can be displayed on a display along with the evidence for evaluation. Here, the evidence for evaluation includes, for example the strain graph, the instability graph and evaluation result of the pressing operation. In this manner, it is possible to select the elastic image generated under stable compression.

Further, a certain section having the smaller difference of the feature quantities than a preset threshold value is extracted, and the elastic image generated on the basis of the elastic frame data of the extracted section is evaluated as high image quality. In this manner, the elastic image generated in the condition with adequate pressing operation can be evaluated as having high image quality.

The ultrasonic diagnostic apparatus for executing the method for evaluating image quality of elastic images related to the present invention comprises:

a probe configured to transmit/receive ultrasonic waves to/from an object;

a displacement measuring unit configured to calculate plural sets of displacement frame data showing the distribution of the displacement of biological tissue on the basis of the plural sets of RF signal frame data acquired by activating the probe;

an elasticity information calculating unit configured to calculate the plural sets of elastic frame data showing the distribution of the elasticity information on the basis of the displacement frame data;

an elastic image constructing unit configured to generate an elastic image in the scan plane on the basis of the elastic frame data; and a display configured to display the elastic image.

The ultrasonic diagnostic apparatus of the present invention is characterized in comprising an elastic image evaluating unit configured to detect the fluctuation cycle of the displacement of the plural sets of displacement frame data or the elasticity information of the plural sets of elastic frame data, acquire the feature quantity of the fluctuation pattern of the displacement or the elasticity information for each predetermined section in the fluctuation cycle, and evaluate the image quality of the elastic image on the basis of the variation of the feature quantity.

Or in place of this, the ultrasonic diagnostic apparatus of the present invention can be provided with an elastic image evaluating unit configured to detect the fluctuation cycle of the displacement of the plural sets of displacement frame data or the elasticity information of the plural sets of elastic frame data, acquire the feature quantity of the fluctuation pattern of the displacement or the elasticity information for each predetermined section in the fluctuation cycle, acquire the difference between the feature quantity of a certain section and the feature quantity of another one or plural sections which are detected in prior to the certain section, and evaluate the image quality of the elastic image on the basis of the difference of the feature quantities.

In this manner, in accordance with the ultrasonic diagnostic apparatus of the present invention, it is possible to evaluate stability of the pressing operation, make a stable evaluation of elastic images, and select the elastic image with high reliability and accuracy which is adequate for making a proper diagnosis. Also, all of the characteristics related to the method for evaluating the image quality of elastic images in the present invention can be applied to the ultrasonic diagnostic apparatus.

Effect of the Invention

In accordance with the present invention, it is possible to evaluate the image quality of elastic images appropriately with high reliability and accuracy.

DETAILED DESCRIPTION OF THE INVENTION

Figure 1:
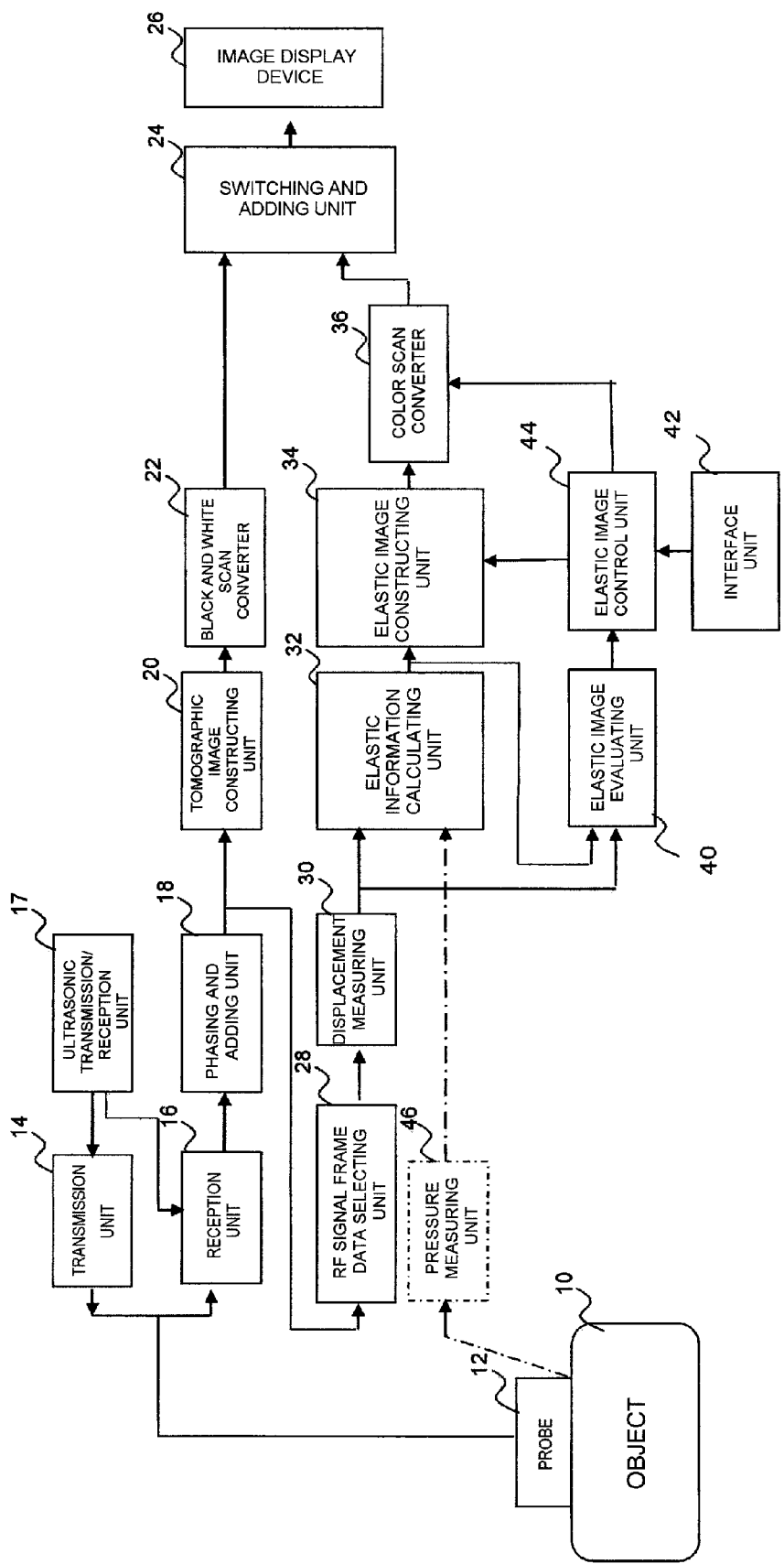
FIG. 1 is a block configuration diagram of the ultrasonic diagnostic apparatus in a first embodiment of the present invention.

An embodiment of the ultrasonic diagnostic apparatus for executing the method of evaluating the image quality of elastic images related to the present invention is configured as shown in the block diagram of FIG. 1.

As shown in the diagram, the ultrasonic diagnostic apparatus comprises a probe 12 which is to be used by applying to an object 10. The probe 12 is provided with a plurality of transducers arrayed therein for transmitting/receiving ultrasonic waves to/from the object 10. The probe 12 is activated by the ultrasonic waves output periodically from a transmission unit 14.

The transmission unit 14 generates a transmission pulse for producing an ultrasonic wave by activating the probe 12, and sets the convergent point of the transmitted ultrasonic waves at a certain depth. In this manner, an ultrasonic beam is periodically scanned from the probe 12 on the scanned plane of the object 10. The RF signals which are reflected from the biological tissue in the scanned plane of the object 10 and received by the probe 12 is processed by being amplified at a certain gain by a reception unit 16, phased and added in a phasing and adding unit 18, and the RF signal frame data is generated. The RF signal frame data output from the phasing and adding unit 18 is input to a tomographic image constructing unit 20 and an RF signal frame data selecting unit 28.

The tomographic image constructing unit 20 performs signal processing such as the gain compensation, log compression, detection, edge enhancement and filtering on the input RF signal frame data, constructs a grayscale tomographic image, for example a black and white tomographic image of the scanned plane, and outputs the image to a black and white scan converter 22. The black and white scan converter 22 is configured including an A/D converter configured to convert the input tomographic image data into digital signals, a frame memory configured to store the converted plural sets of tomographic image data in time series, and a controller.

Also, the black and white scan converter 22 obtains the frame data of a tomographic image which is stored in the frame memory as one image, reads out the frame data of the obtained tomographic image with TV, and converts the frame data in the manner to accord with the display method of an image display device 26.

The RF signal frame data selecting unit 28 sequentially stores the plural sets of RF signal frame data that are consecutively output from the phasing and adding unit 18, selects the two sets of RF signal frame data having the different acquisition times, i.e. different pressures according to the commands input from the control unit (not shown in the diagram) of the ultrasonic diagnostic apparatus, and outputs the selected data to a displacement measuring unit 30. In concrete terms, the RF signal frame data selecting unit 28 selects RF signal frame data (N) as a first data set from among the stored sets of RF signal frame data, at the same time as selecting one set of RF signal frame data (X) from among the RF signal frame data group (N-1, N-2, N-3, . . . N-M) that are stored temporally in the past. Here, N, M and X are the index numbers given to the RF signal frame data, and are positive integers.

The displacement measuring unit 30 performs one-dimensional or two-dimensional correlation processing on selected sets of data, i.e. the RF signal frame data (N) and the RF signal frame data (X), and obtains one-dimensional or two-dimensional displacement distribution related to the displacement caused by the difference of applied pressure in the respective portions of the biological tissue in the object 10 or the moving vector, i.e. the direction and size of the displacement. Then the displacement measuring unit 30 generates the displacement frame data which represents the displacement distribution in the respective portions, and outputs the generated data to an elasticity information calculating unit 32. Here, the block matching method is used for detecting the moving vectors. The block matching method divides an image into the blocks formed by, for example N×N pixels, focuses on the block within a region of interest, searches the most approximated block to the focused block from the previous frames, and determines the sample value based on the predictive coding, i.e. the difference by referring to the searched block.

The elasticity information calculating unit 32 generates by calculation the plural sets of elastic frame data which represent the distribution of elasticity information (the strain or the elasticity modulus) that shows hardness and softness in the respective portions of the biological tissue in the scanned plane on the basis of the displacement frame data output from the displacement measuring unit 30, and outputs the generated data to an elastic image constructing unit 34.

In other words, the elasticity information calculating unit 32 calculates the strain in the biological tissue corresponding to the respective points on a tomographic image on the basis of the displacement frame data, for example the moving vectors output from the displacement measuring unit 30, and generates the elastic frame data which represents the distribution of the acquired strain. The data of strain is calculated by performing the spatial differentiation on the moving distance, for example the displacement of the biological tissue.

Also, the elasticity information calculating unit 32 is capable of generating the elastic frame data which represents the distribution of elasticity modulus based on the data of strain. In this case, a pressure measuring unit 46 shown in FIG. 1 is necessary. The pressure measuring unit 46 measures the pressure in the respective portions of the scanned plane using the pressure values detected by a pressure sensor placed between the probe 12 and the object 10. Then the elasticity information calculating unit 32 calculates the distribution of elasticity modulus by dividing the variation of pressure output from the pressure measuring unit 46 by the variation of strain.

For example, when the displacement measured by the displacement measuring unit 30 as L(X) and the pressure measured by the pressure measuring unit 46 as P(X), the strain $\Delta S(X)$ can be calculated by performing the spatial differentiation on L(X). In other words, the strain can be calculated using the equation: $\Delta S(X) = \Delta L(X)/\Delta X$. Also, the Young's modulus Ym(X) of elasticity modulus data can be calculated by the equation: $Ym = (\Delta P(X))/\Delta S(X)$. The elasticity modulus of the biological tissue corresponding to the respective points in the tomographic image can be obtained from this Young's modulus Ym.

The Young's modulus is the proportion of the simple tensile stress applied to a subject with respect to the distortion generated in parallel to the stress. In this manner, the elasticity information calculating unit 32 is capable of consecutively acquiring the elastic frame data which is the two-dimensional distribution of the elasticity information that is the strain or the elasticity modulus.

The elastic image constructing unit 34 is formed by a frame memory and an image processing section, to save the elastic frame data output from the elasticity information calculating unit 32 in time series in the frame memory, perform image processing with respect to the saved elastic frame data, generates elastic image data in the scanned plane and outputs the generated data to a color scan converter 36. The color scan converter 36 constructs a color elastic image to which the hue is given in accordance with the value of the elasticity information of the input elastic image data.

That is, the elasticity information is converted into the light's three primary colors, i.e. red (R), green (G) and blue (B) on the basis of the elastic frame data, and the color elastic image is converted so as to be coincided with the display method of the image display device 26. For example, the elasticity information with large strain is converted into the red code, and the elasticity data with small strain is converted into the blue code.

A switching and adding unit 24 comprises a frame memory, an image processing section and an image selecting section. A frame memory is for storing the tomographic image data from the black and white scan converter 22 and the color elastic image data from the color scan converter 36. Also, the image processing section, in accordance with the command from the control unit of the ultrasonic diagnostic apparatus which is not shown in the diagram, on the basis of the tomographic image data and the color elastic image data that are stored in the frame memory, performs image processing of superimposing the images, juxtaposing the images or changing the composite ratio of the synthetic images. The luminance information and hue information of the respective pixels of the composite image is acquired by adding each piece of information of the black and white tomographic image and the color elastic image at the composite ratio.

Also, the image selecting unit selects an image to be displayed on the image display device 26 from among the tomographic image data and the elastic image data in the frame memory and the composite image data in the image processing section, and displays a composite image on the image display device 26.

Here, the configuration of characteristic components in the ultrasonic diagnostic apparatus of the present embodiment will be described. The present embodiment is characterized in comprising an elastic image evaluating unit 40, an interface unit 42 and an elastic image control unit 44. The elastic image evaluating unit 40 evaluates the image quality of an elastic image on the basis of the displacement frame data output from the displacement measuring unit 30 or the elastic frame data output from the elasticity information calculating unit 32. The elastic image control unit 44 controls the elastic image evaluating unit 40, elastic image constructing unit 34 and the color scan converter 36, based on the commands input from the interface unit 42.

The elastic image evaluating unit 40 consecutively loads the displacement frame data output from the displacement measuring unit 30 or the elastic frame data output from the elasticity information calculating unit 32, and detects the fluctuation cycles of the displacement or the elasticity information. Then the elastic image evaluating unit 40 acquires the feature quantity of the fluctuation pattern in the displacement or the elasticity information in the respective sections, while setting each of a half cycle of the fluctuation cycle as a section. Next, the elastic image evaluating unit 40 acquires the difference between the feature quantity of a certain section and the feature quantity of another one or plural sections that are detected prior to the certain section, and evaluates whether or not the image quality of the elastic image generated from the elastic frame data in the certain section is high, based on the difference between the feature quantities and the image evaluation disclosed in JP-A-2005-118152. In short, the elastic image evaluating unit 40 detects the fluctuation cycle of the displacement or the elasticity information, acquires the feature quantity of the fluctuation pattern of the displacement or the elasticity information for each section of a half cycle of the fluctuation cycle, and evaluates whether or not the image quality of the elastic image generated from the elastic frame data corresponding to each section is high based on the variation of the feature quantities in plural sections, i.e. based on the stability of the variation of the feature quantities.

In the case of obtaining an elastic image, the operation to move the probe 12 from the initial condition that a certain initial pressure (including zero) is applied by the probe 12 from the body surface of the object 10 to a region of interest in the direction to press the probe 12 toward the region of interest and the operation to move the probe in the direction to release the probe away from the region of interest are repeated. In other words, on the basis of the initial condition that pressure is added to a region of interest, increase and decrease of the pressure is repeated. The operation to add pressure to a region of interest of the object 10 by the probe 12 fluctuates depending on the size of the stroke, the velocity, the direction and the like of the pressing and releasing operation of the probe 12. Therefore, elastic images with much noise that are obtained with improper pressing operation end up being mixed in the consecutively obtained plural pieces of elastic images.

In the present embodiment, the elastic image evaluating unit 40 evaluates the stability of pressing operation, i.e. the stability of the elastic image in a predetermined section, and evaluates the image quality of the elastic image with high reliability and accuracy for making a proper diagnosis. The method for evaluating image quality of elastic images in the elastic image evaluating unit 40 will be described below in different embodiments.

Embodiment 1

Figure 2:
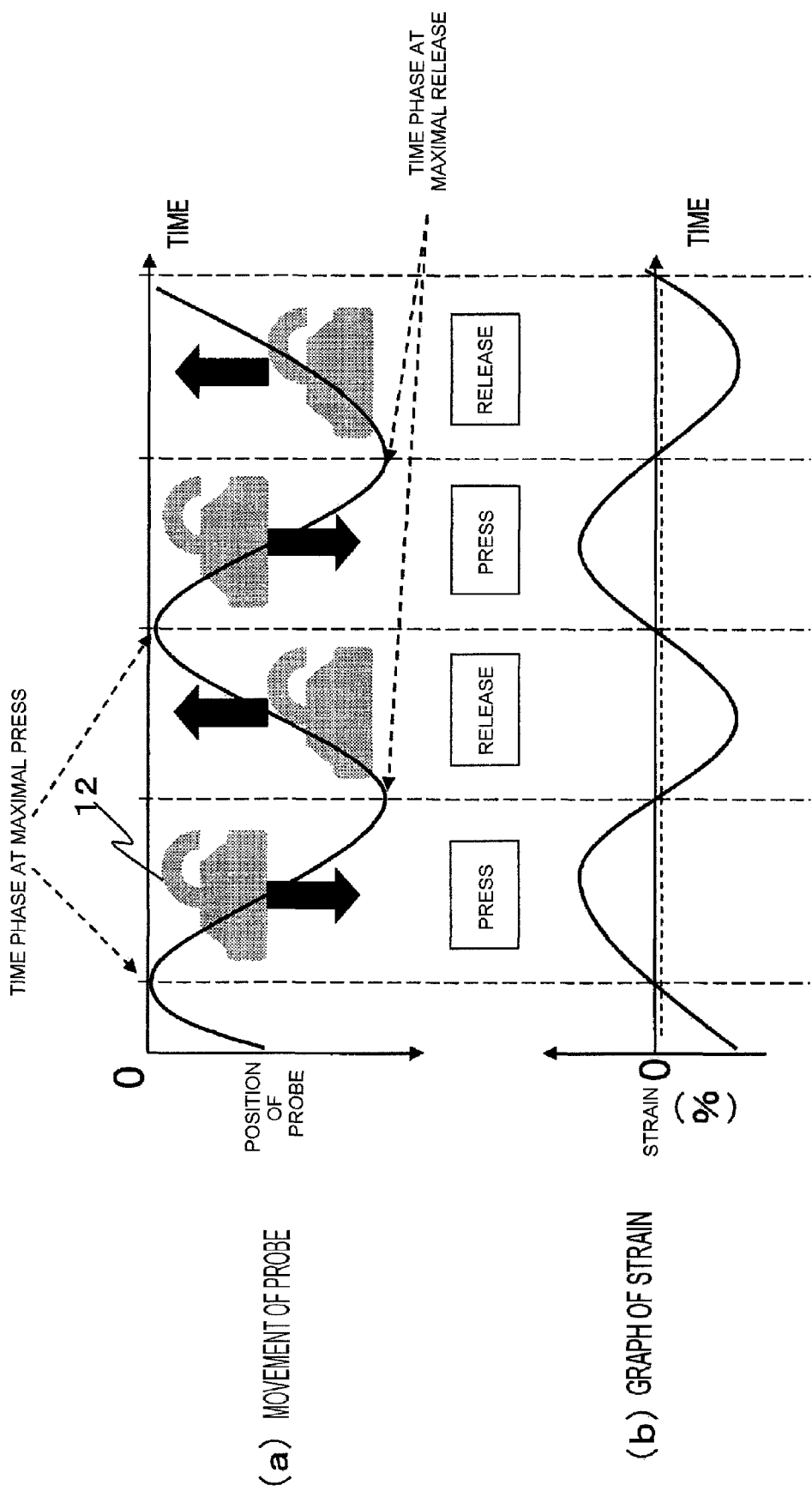
FIG. 2 is a graph showing an example of pressing operation and the fluctuation cycle of the strain corresponding to the pressing operation, for explaining the first embodiment of the present invention.

FIG. 2 shows graphs for explaining the first embodiment indicating an example of pressing operation and fluctuation cycles of the strain corresponding to the pressing operation. FIG. 2(a) shows the time change of the movement indicating positional change of the probe 12 caused by pressing operation. As shown in the diagram, the probe 12 repeats, for example the pressing and releasing operation performed manually by an examiner with respect to the object 10. The example in the diagram is a comparatively ideal sine-wave patterned pressing operation performed by the same strokes as shown in the diagram, wherein the local maximum point in the upper part of the diagram indicates the time phase at the maximum releasing operation of the probe 12 and the local minimum point in the lower part indicates the time phase at the maximum pressing of the probe 12.

While the body-surface position of the object 10 is set as the initial condition (pressure=0) at the maximum release position of the probe 12 in this example, the present invention is not limited to this. The position where a certain initial pressure is applied to the object 10 by the probe 12 (for example, the position with 2~10% strain) can be set as the initial condition. Corresponding to such movement of the probe 12, the strain (%) as shown in FIG. 2(b) is generated in the biological tissue of a region of interest in the object 10 to which the pressure is added. As shown in the diagram, though the phase of strain is delayed with respect to the movement of the probe 12, the fluctuation cycles of the strain are stable corresponding to the ideal sine-wave patterned pressing operation.

Figure 3:
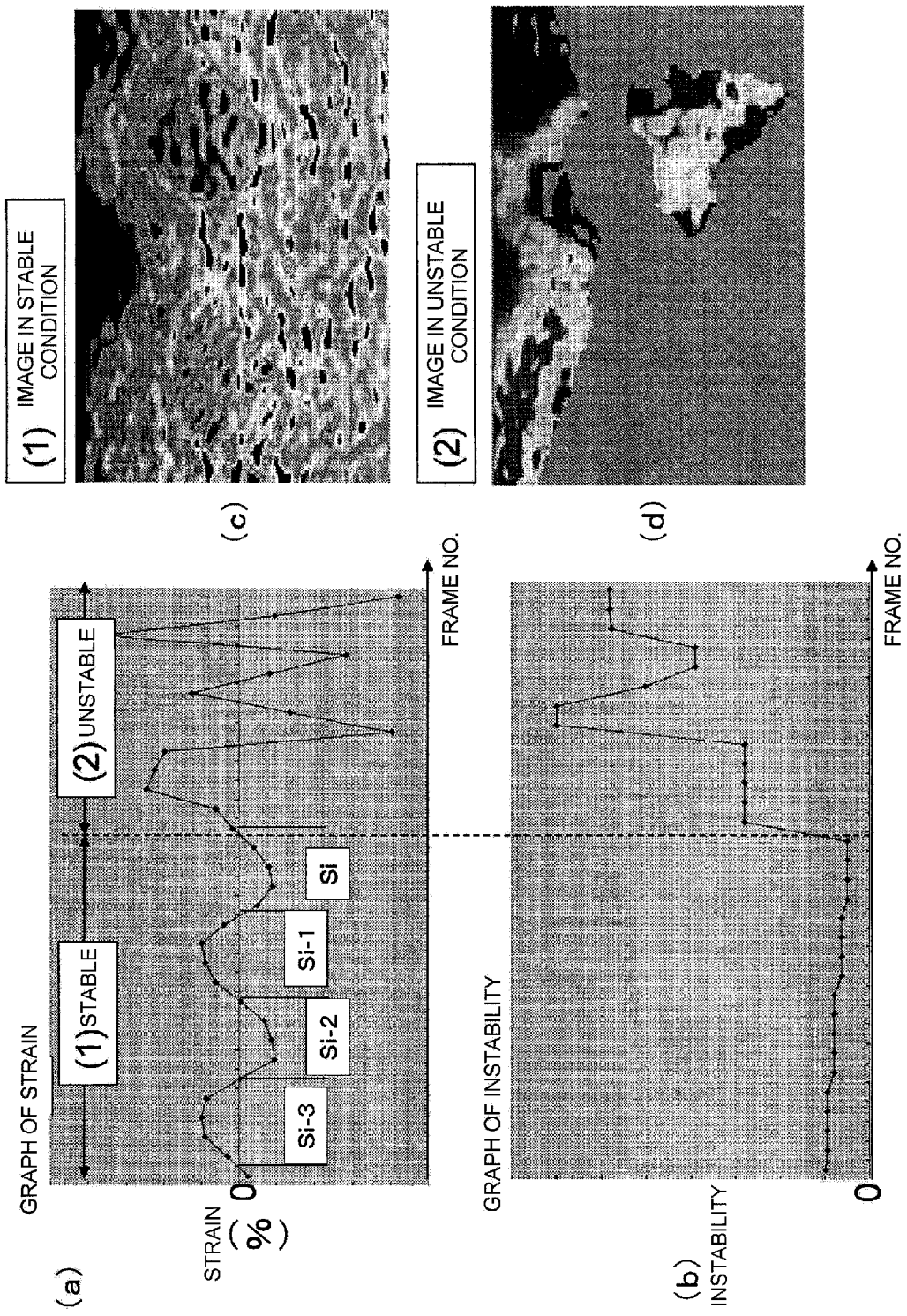
FIG. 3 is a view for explaining the method of evaluating the image quality of elastic images in the first embodiment of the present invention.

FIG. 3 shows the case that the fluctuation cycles of strain are stable and the case that the fluctuation cycles of stain are unstable due to the movement of the probe 12, for comparison. In FIG. 3(a), the left side shows the case that the fluctuation cycles of strain are stable, and the right side shows the case that the fluctuation cycles of strain are unstable. In the diagram, while the lateral axis indicates the time axis, the black points on the graph correspond to the frame No. of the elastic frame data. In other words, the graph shows that the plural sets of elastic frame data are obtained during each cycle of the pressing and releasing operation of the probe 12 shown in FIG. 2. FIG. 3(b) is an instability graph which is acquired in accordance with the equation of instability to be described later, corresponding to the stability and the instability of the fluctuation cycles of strain.

From the diagram, a pattern can be recognized that the instability is low when the fluctuation of strain is stable and continued in sine-waved pattern and the instability is high when the fluctuation cycles of strain are greatly derived from the sine-waved pattern and consecutively unstable.

Also, the elastic image obtained in the condition that the fluctuation pattern of strain is consecutively stable in a sine-wave pattern has high quality with less noise as shown in FIG. 3(c). On the other hand, the elastic image obtained in the condition that the fluctuation pattern of strain is unstable has low image quality with much noise as shown in FIG. 3(d). In FIG. 3(d), the region shown in the center part with uniform pattern is the region where the elasticity information is cut off in the process of the elasticity information calculating unit 32 due to much noise.

The ultrasonic diagnostic apparatus in the first embodiment comprises a probe 12 configured to transmit/receive ultrasonic waves to/from an object, an elasticity information calculating unit 32 configured to calculate the elasticity information on the basis of the ultrasonic waves received by the probe 12, an elastic image constructing unit 34 configured to construct an elastic image on the basis of the elasticity information, and an image display device (display) 26 configured to display the elastic image, characterized in comprising an elastic image evaluating unit 40 configured to detect the fluctuation cycles of elasticity information, acquires the fluctuation pattern of the elasticity information for each predetermined section of the fluctuation cycles, and evaluate the stability of an elastic image on the basis of the fluctuation pattern. The elastic image evaluating unit 40 causes the elastic image evaluated as having high image quality in the predetermined section having high stability of the fluctuation cycle to be displayed on the image display device (display) 26. The elastic image evaluating unit 40 further acquires the proportion of the noise region included in the elastic image in the predetermined section having high stability, and causes the elastic image having the smallest proportion of the noise region to be displayed on the image display device (display) 26.

Figure 4:
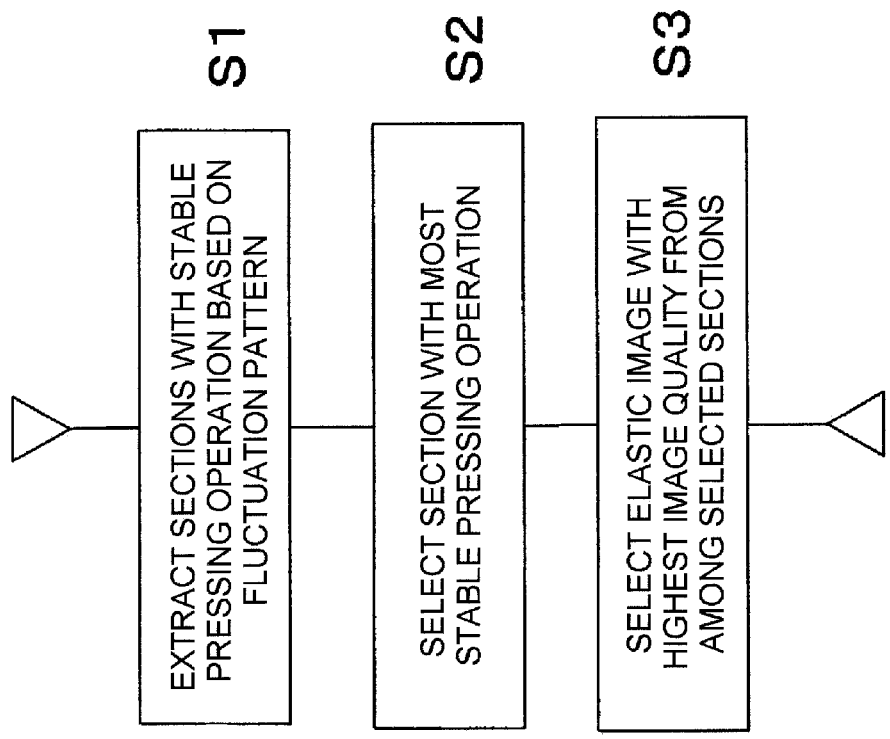
FIG. 4 is a flowchart showing the procedure of the method for evaluating the image quality of elastic images in the first embodiment of the present invention.

In concrete terms, as shown in the flowchart of FIG. 4, the elastic image evaluating unit 40 is configured comprising a first stage for evaluating the stability of pressing operation which influence the image quality of elastic images on the basis of the fluctuation pattern of the elastic frame data of the strain output from the elasticity information calculating unit 32 in accordance with the above-described principle, and a second stage for evaluating the image quality of an elastic image which is the conventional technique disclosed in JP-A-2005-118152 and so on.

As shown in FIG. 4, the first stage has steps S1 and S2. In the first stage, the fluctuation cycles of the strain which are the elasticity information of the consecutively input plural sets of elastic frame data are detected, and evaluation is made whether or not the image quality of an elastic image is a certain value or higher depending on whether or not the fluctuation pattern of the consecutive fluctuation cycles is stable.

(Step S1)

First, the instability of the fluctuation cycles of strain is obtained. At this time, a region of interest (ROI) is set in each set of elastic frame data, and the average value of the strain in the ROI is set as the representative value of the strain in the elastic frame data. In this manner, the graph of the fluctuation cycles of strain as shown in FIG. 3(a) can be obtained. In the first embodiment, the stability or the instability of strain is obtained depending on whether or not the fluctuation pattern strain in the consecutive plural half-cycles is stable. More specifically, in the strain graph of FIG. 3(a), each of the half cycle in the fluctuation cycles is set as section Si on the basis of strain 0(%). Here, "i" is a certain section which is considered as the evaluation target, and another one or plural sections detected prior to this certain section are set as S(i–m). In this case, "i" is a whole number, and "m" is the whole numbers of 1, 2, . . . , N.

Figure 5:
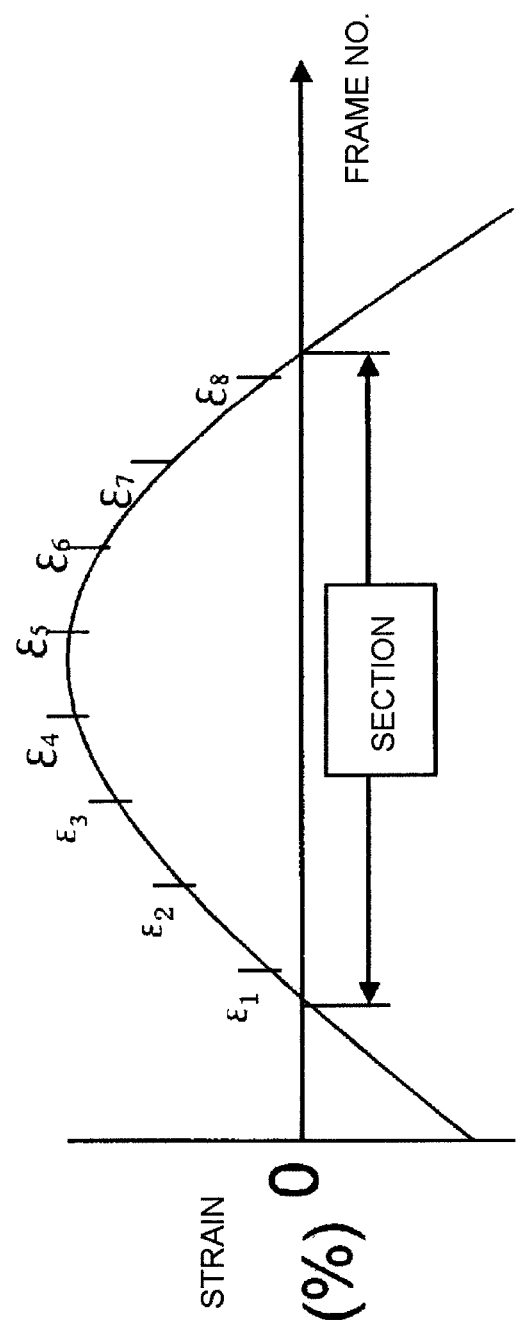
FIG. 5 is a view for explaining the method of acquiring the standard deviation which is an example of the feature quantity of the fluctuation pattern in the first embodiment of the present invention.

Next, the present embodiment uses the standard deviation of the half cycles of strain shown in FIG. 5 as the feature quantity of the fluctuation of strain or the fluctuation pattern of the half cycles. In FIG. 5, it is assumed that the number of elastic frame sets in section Si is "k". When the strain of each set of elastic frame data is set as "$\epsilon j$", the average value "$\epsilon$ mean" of the strain in section Si can be expressed by the following equation (1), thus the standard deviation $\sigma i$ of the strain in section Si can be expressed by the following equation (2).

$$\epsilon\text{mean}=1/k\cdot\Sigma\epsilon j \qquad (1)$$

$$\sigma i=\sqrt{\{1/k\cdot\Sigma(\epsilon j-\epsilon\text{mean})^2\}} \qquad (2)$$

In this manner, standard deviation $\sigma(i-m)$ of the strain in another one or plural sections $S(i-m)$ that are detected prior to section Si can be obtained. Then the difference between the standard deviation $\sigma i$ of the strain in section Si and the standard deviation $\sigma(i-m)$ of the strain in another one or plural standard deviations $\sigma(i-m)$ is obtained. Further, when the number of sections for obtaining the difference between the standard deviation in section Si and the standard deviation $\sigma(i-m)$ is set as N, the instability of pressure in the section Si can be expressed in the following equation (3).

$$\text{Instability of Section } Si=1/N\cdot\Sigma(\sigma i-\sigma(i-m)) \qquad (3)$$

In the equation (3), it is not preferable to increase the number of sections N, since the difference of instability between section Si which is the evaluation target and the other sections $S(i-m)$ becomes small. Given this factor, it is preferable to set, for example about 3~5 as N.

Next, by comparing the obtained instability in section Si and a predetermined steady value, in the case that the instability is the steady value or smaller, the evaluation is made that the image quality of the elastic image generated by the strain distribution of the elastic frame data corresponding to the same section Si is high. Then the sections having the instability of the steady value or smaller are sequentially extracted.

(Step S2)

In step S2, the section having the lowest instability in manual pressing operation is selected from among the extracted plural sections having the instability of the steady value or smaller.

(Step 3)

Step S3 is the evaluation of image quality in the second stage. More specifically, as shown in FIG. 3(a), even in the section having the lowest instability of manual pressing operation, the image quality of the elastic image does not always turn out as high in the elastic frame data of the case, for example that the strain $\epsilon$ is close to 0%. Given this factor, the elastic image evaluating unit 40 applies the method for evaluating image quality of elastic images disclosed in JP-A-2005-118152, and selects the elastic frame data having, for example high image quality from among the sets of elastic frame data in section Si on the basis of the elastic frame data in the section Si which is evaluated as having high image quality. As an example, image data can be evaluated as follows with respect to the pixel data $Xi,j$ (i=1, 2, 3, . . . , N and j=1, 2, 3, . . . , M) of the entire region or a region of interest of elastic frame data. Centering around the pixel position of a evaluation target, a kernel of, for example 3×5 pixel size is set, a total of 15 pixel data groups that are distributed in the kernel is set as a population, and for example, the average or the standard deviation of the elasticity values is obtained as the statistical feature quantity of the population and as the image quality evaluation value. Then with respect to the pixel data $Xi,j$ in the entire region or a region of interest of the elastic frame data, the image evaluation value is obtained for each set of data, and the image quality frame data is created. This image frame data shows the fluctuation of the elasticity value of pixels in the evaluation target with respect to the population of the kernel size.

Therefore, even when there are pixels of the evaluation target having the smaller image quality evaluation value than a threshold value, if the proportion of the pixels thereof is small in the entire region or the region of interest, the elastic image can be evaluated as having high quality.

Given this factor, for example in step S3, the pixels having the strain in the respective measurement points (pixels) in the entire region or a region of interest (ROI) of the elastic frame data is smaller than a first threshold value compared to the strain of the average or the standard deviation in the kernel are obtained. Then the proportion in which the pixels having smaller strain than the first threshold value occupy in the entire region or the ROI is acquired. When this proportion is great, the elastic image is evaluated as having low image quality, and the elastic image is eliminated from the selection. Further, even elastic frame data which remains in the selection, if there is a region in which the strain is generated in the direction opposite from the pressing direction in the entire region or the region of interest, and the proportion of the region which occupies in the entire region or the region of interest is greater than a second threshold value, the elastic image is evaluated as having low image quality and is eliminated from the selection. In this manner, the elastic frame data in the section Si which is evaluated as having high stability of pressing operation and high image quality is further evaluated by another image evaluation standard, and the elastic image corresponding to the elastic frame data having the highest evaluation value is selected. Then by automatically displaying the selected elastic image on the image display device 26, an examiner can obtain the elastic image which is appropriate for making a proper diagnosis easily and quickly.

Figure 6:
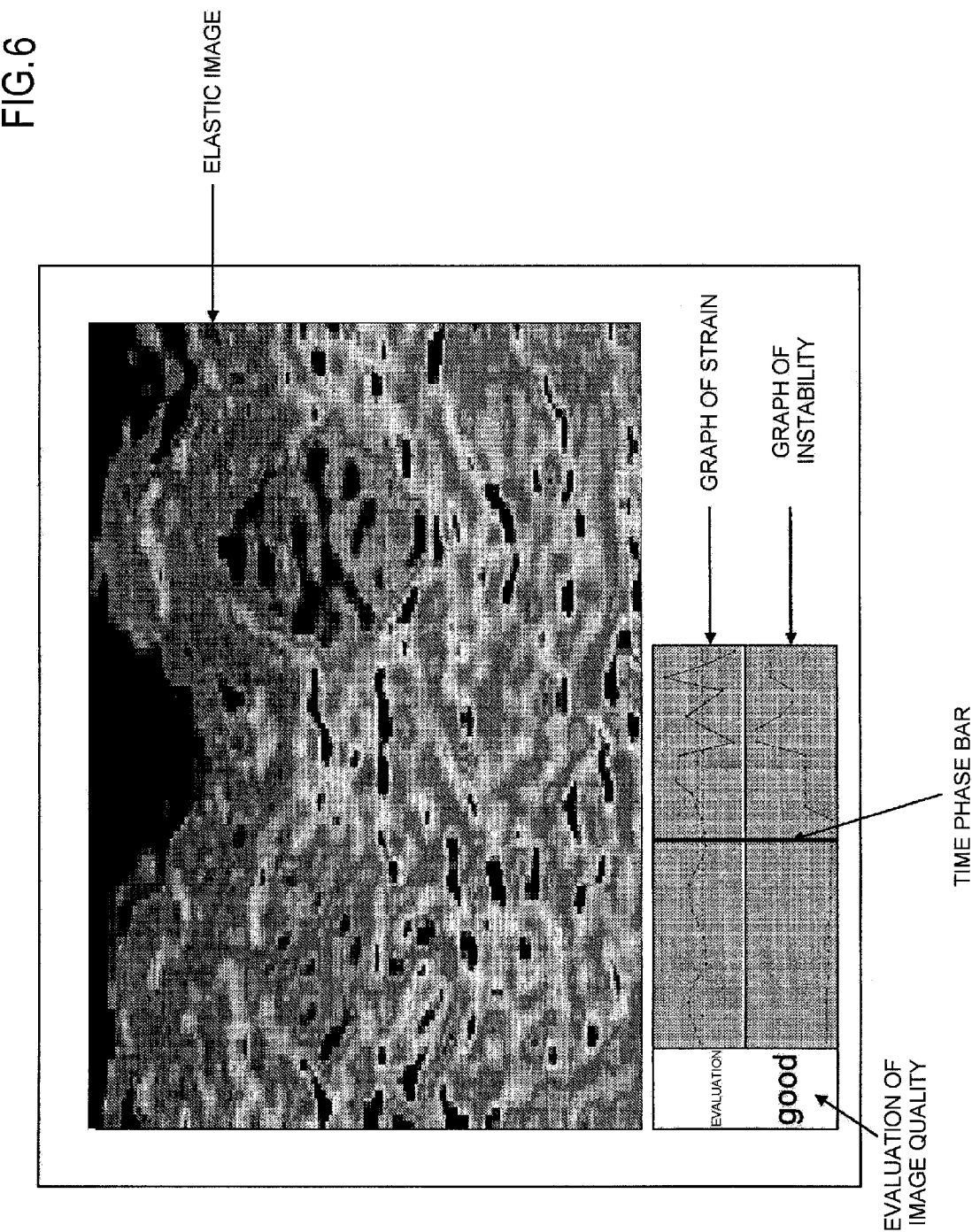
FIG. 6 is an example of an elastic image obtained by applying the method for evaluating the image quality of elastic images and the display example of the information related to the image quality evaluation of the elastic image in the first embodiment of the present invention.

FIG. 6 shows a display example of the elastic image obtained by the method for evaluating image quality of elastic images in the first embodiment.

As shown in the diagram, an elastic image having high image quality and the evaluation thereof are displayed, and the strain graph showing the fluctuation cycles of the strain which is similar to the graph as shown in FIG. 3 for showing the reason for the evaluation is displayed side by side with the instability graph corresponding to the strain graph. Especially, by moving a time phase bar which is displayed in these graphs in the time axis direction, the elastic image and the evaluation thereof are displayed in the indicated time phase.

As described above, in accordance with the first embodiment, since the stability of pressing operation is evaluated on the basis of the variation of the feature quantity in the fluctuation pattern of the elasticity information in the elastic frame data acquired by the result of the pressing operation, it is possible to make stable evaluation of the image quality of the elastic images appropriate for making a diagnosis and to select the elastic images with high reliability and accuracy for making a proper diagnosis. In addition, the elastic image evaluating unit 40 can be configured by a computer and operated by a program of the computer, for executing the method to evaluate image quality of elastic images.

While the standard deviation is used for the feature quantity of the fluctuation pattern of strain in each section in the first embodiment, the present invention is not limited to this. The average value, the area or the dispersion of fluctuation pattern of the strain in each section, can also be used. Also, while an example to use the strain as the elasticity information of elastic frame data is described, the elasticity modulus can be used instead to achieve the same effect.

Embodiment 2

In the first embodiment, the image quality of elastic images is evaluated by whether or not the pressing operation is stable using the pattern of the fluctuation cycles in the elasticity information of elastic frame data. Since the image quality is evaluated in the first embodiment by the fluctuation pattern of the elasticity information which is directly related to the image quality of the elastic image, the accuracy and reliability of the evaluation is high. However, the present embodiment is instead capable of evaluating the image quality by whether or not manual pressing operation is stable using the fluctuation pattern of the displacement frame data in which the movement of the pressing operation is measured by the displacement measurement unit 30.

Embodiment 3

Also in step S3 of the first embodiment, the proportion is obtained wherein the region having the strain E, which is smaller than the first threshold value, of the respective measurement points (pixels) in the entire region or a region of interest (ROI) of the elastic frame data occupies the entire region or the ROI. And the image quality of the elastic image is evaluated in accordance with the obtained proportion. However, the present embodiment is instead capable of executing the similar processing using the elasticity modulus of the respective measurement points (pixels) for evaluating the image quality of the elastic image. The present embodiment is also capable of obtaining the proportion in which the region having the displacement, which is smaller than a threshold value, in the respective measurement points in the entire region or a region of interest of the displacement frame data occupies the entire region or the region of interest, and evaluating the image quality in accordance with the obtained proportion. Further, the elastic image evaluating unit 40 is configured to load two sets of RF signal frame data output from the RF signal frame data selecting unit 28 so as to evaluate the image quality of the elastic image.

Embodiment 4

The present embodiment is capable of storing elastic images with high quality that are obtained in the above-described respective embodiments 1~3 in a memory such as a sine memory. In this manner, it is possible to regenerate the elastic images with high quality that are stored in the memory for making a proper diagnosis.

DESCRIPTION OF REFERENCE NUMERALS

10: object
12: ultrasonic probe
14: transmission unit
16: reception unit
17: ultrasonic transmission/reception control unit
18: phasing and adding unit
20: tomographic image constructing unit
22: black and white scan converter
24: switching and adding unit
26: image display device
28: RF signal frame data selecting unit
30: displacement measuring unit
32: elasticity information calculating unit
34: elastic image constructing unit
36: color scan converter
40: elastic image evaluating unit
42: interface
44: elastic image control unit
46: pressure measuring unit

The invention claimed is:
1. An ultrasonic diagnostic apparatus comprising:
a probe configured to transmit/receive ultrasonic waves to/from an object to be examined;
an elasticity information calculating unit configured to calculate elasticity information based on the ultrasonic waves received by the probe;
an elastic image constructing unit configured to generate a plurality of elastic image frames based on the elasticity information;
a display configured to display the plurality of elastic image frames; and
an elastic image evaluating unit configured to:
  detect fluctuation cycles of the elasticity information, wherein the fluctuation cycles are produced by pressing the probe toward the region of interest and releasing the probe away from the region of interest,
  divide the plurality of elastic image frames into a plurality of groups, wherein each group of the plurality of groups includes a plurality of frames,
  calculate a feature quantity of the each group by using respective data,
  obtain an instability of the respective groups based on differences of feature quantities between a certain group and one or a plurality of groups that are detected prior to the certain group,
  evaluate elastic images of the respective groups by making a score of the elastic images having a small instability higher than a score of the elastic images having a large instability,
  generate a strain graph with the fluctuation pattern of the elasticity information, an instability graph and a movable time phase bar, and
  detect the movable time phase bar displayed in the strain graph with the fluctuation pattern and the instability graph in a time axis direction,
  wherein the elastic images and an evaluation of the elastic images are displayed in a time phase indicated by the movable time phase bar.

2. The ultrasonic diagnostic apparatus according to claim 1, wherein the elastic image evaluating unit causes an elastic image which is evaluated as having high quality in a section predetermined to have high stability in the fluctuation cycles to be displayed on the display.

3. The ultrasonic diagnostic apparatus according to claim 1, wherein the elastic image evaluating unit further obtains the proportion of a noise region included in an elastic image in a section predetermined to have high stability, and causes the elastic image having the smallest proportion of the noise region to be displayed on the display.

4. The ultrasonic diagnostic apparatus according to claim 1, wherein the elastic image evaluating unit obtains the fluctuation pattern of the elasticity information for each predetermined section of the fluctuation cycles, acquires a difference between a feature quantity in a certain section and a feature quantity in another one or a plurality of sections that are detected prior to the certain section, and evaluates an image quality of an elastic image based on the difference of the feature quantities.

5. The ultrasonic diagnostic apparatus according to claim 4, wherein the elastic image evaluating unit extracts a certain section having the smallest difference of the feature quantities compared to a preset threshold value, and determines the elastic image of the certain extracted section as having high image quality.

6. The ultrasonic diagnostic apparatus according to claim 1, wherein the fluctuation cycles are the fluctuation of the average value of the displacement, the strain, or the elasticity modulus in a region of interest set in an elastic image.

7. The ultrasonic diagnostic apparatus according to claim 1, wherein the fluctuation pattern of the elasticity information in respective sections is the average value or the standard deviation of the fluctuation in the elasticity information in the respective sections.

8. A method of evaluating image quality of elastic images, the method comprising:

transmitting/receiving, to/from a probe, ultrasonic waves to/from an object to be examined;

calculating elasticity information based on the ultrasonic waves received by the probe;

generating a plurality of elastic image frames based on the elasticity information;

displaying on a display the plurality of elastic image frames;

detecting fluctuation cycles of the elasticity information, wherein the fluctuation cycles are produced by pressing the probe toward the region of interest and releasing the probe away from the region of interest, dividing the plurality of elastic image frames into a plurality of groups, wherein each group of the plurality of groups includes a plurality of frames, calculating a feature quantity of the each group by using respective data, obtaining an instability of the respective groups based on differences of feature quantities between a certain group and one or a plurality of groups that are detected prior to the certain group, evaluating elastic images of the respective groups by making a score of the elastic images having a small instability higher than a score of the elastic images having a large instability, generating a strain graph with the fluctuation pattern of the elasticity information, an instability graph and a movable time phase bar;

detecting the movable time phase bar displayed in the strain graph with the fluctuation pattern and the instability graph in a time axis direction; and displaying the elastic images and an evaluation of the elastic images in a time phase indicated by the movable time phase bar.

9. The method for evaluating image quality of elastic images according to claim 8, further comprising:

displaying on a display an elastic image determined to have high quality in a section predetermined to have high stability in the fluctuation cycles.

10. The method for evaluating image quality of elastic images according to claim 8, further comprising:

obtaining the proportion of a noise region included in the elastic image in a section predetermined to have high stability; and displaying on the display the elastic image having the smallest proportion of noise region.

\* \* \* \* \*